United States Patent [19]
Tzianabos et al.

[11] Patent Number: 5,679,654
[45] Date of Patent: Oct. 21, 1997

[54] CAPSULAR POLYSACCHARIDE IMMUNOMODULATOR

[75] Inventors: Arthur O. Tzianabos, Reading; Andrew B. Onderdonk, Westwood; Dennis L. Kasper, Newton Center, all of Mass.

[73] Assignee: Brigham & Women's Hospital, Inc., Boston, Mass.

[21] Appl. No.: 301,271

[22] Filed: Sep. 2, 1994

[51] Int. Cl.$^6$ .................. A61K 31/715; A61K 31/725; A61K 31/73; A61K 39/02
[52] U.S. Cl. .................. 514/54; 424/831; 514/56; 514/61; 536/18.7; 536/123; 536/123.1
[58] Field of Search .................. 514/54, 885, 55–62; 536/18.7, 123.1, 123, 123.12, 123.13, 29.1; 424/831; 530/391, 403, 405

[56] References Cited

U.S. PATENT DOCUMENTS 5,158,939  10/1992  Takayama et al. .................. 514/53
5,576,002  11/1996  Jennings et al. .................. 424/197.11

OTHER PUBLICATIONS

Tzianabos, A. et al., Structural basis for polysaccharide-mediated protection against intraabdominal abscess formation., Biological Abstracts 97:abstract No. 343438.

Tzianabos, A.O. et al., Structrual features of polysaccharides that induce intra-abdominal abscesses., Science 262:416–419 (1993).

Pantosti, A. et al., Immunochemical characterization of two surface polysaccharides of *Bacteroides fragilis*., Infect Immun. 59(6):2075–2082 (1991).

Baumannn, H. et al., Structural elucidation of two capsular polysaccharides from one strain of *Bacteroides fragilis* using high-resolution NMR spectroscopy., Biochemistry 31(16):4081–4089 (1992).

Tzianabos, A.O. et al., The capsular polysaccharide of *Bacteroides fragilis* comprises two ionically linked polysaccharides., J. Biol. Chem. 267(25):18230–18235 (1992).

Tzianabos, A.O. et al., Structural characteristics of polysaccharides that induce protection against intra-abdominal abscess formation., Infect. Immun. 62(11):4881–4886 (1994).

Tzianabos, A. O. et al., Polysaccharide-mediated protection against abscess formation in experimental intra-abdominal sepsis., J. Clin Invest 92:2727–2731 (1995).

Pavliak, V. et al. Structural elucidation of the capsular polysaccharide of *Bacteroides fragilis* strain 23745M1., Carbohydrate Res 275:333–341 (1995).

Tzianabos, A.O. et al., Structure and function of *Bacteroides fragilis* capsular polysaccharides: Relationship to induction and prevention of abscesses., Clin Infect Dis 20 (Suppl 2);S132–S140 (1995).

Tzainabos A.O. et al., Bacterial structure and functional relation to abcess formation., Infect Agents Dis 3:256–265 (1994).

Tzianabos, A.O. et al., Structure–function relationships of polysaccharide–induced intraabdominal abscesses., Infect Immun 62:3590–3593 (1994).

Crabb, J.H. et al., T cell reguation of *Bacteroides fragilis*–induced intraabdominal abscesses., Rev Infect Dis 12(2):S178–S184 (1990).

Lindberg, A.A., et al., Virulence factors in infections with *Bacteroides fragilis*: Isolation and of capsular polysaccharide and lipopolysaccharide., Scand J Infect Dis 35:45–52 (1982).

Kasper D.L., et al., Surface antigens as virulence factors in infection with *Bacteroides fragilis*., Rev Infect Dis 1:278–290 (1979).

Kasper, D.L. et al., The polysaccharide capsule of *Bacteroides fragilis* subspecies fragilis; Immunochemical and morphologic definition., J Infect Dis 133:79–87 (1976).

Baumann, A. et al., Structural Elucidation of Two Capsular Polysaccharides from One Strain of *Bacteroides fragilis* Using High–Resolution NMR Spectroscopy; Biochem., 31:4081 (1992).

Vann, W. et al., The Structure of the Capsular Polysaccharide (K 5 Antigen) of Urinary–Tract–Infective *Excherischi coli* 010:K5:H4 J. of Biochem. 116:359–364, (1981).

DiFabio et al., Structure of the Capsular Polysaccharide Antigen of Type IV Group B Streptococcus; Can. J. Chem. 67:877 (1989).

Fournier, J.M. et al., Isolation of Type 5 Capsular Polysaccharide From *Staphylococcus aureus*; Ann. Inst. Pasteur/Microbiol. (Paris) 138:561–567 (1987).

Jennings, H.J. et al., Immunochemistry of Groups A, B and C Meningococcal Polysaccharide–Tetanus Toxoid Conjugates, J. Immunol. 123:1011–1018 (1981).

Jennings, H.J. et al., Structure of the Complex Polysaccharide C–Substance from *Streptococcus pneumoniae* Type 1; Biochem. 19:4712–4719 (1980).

Kasper, D. et al., Capsular Polysaccharides and Lipopolysaccharides from Two *Bacteroides fragilis* Reference Strains: Chemical and Immunochemical Characterization; J. Bacter. 153:991–997('83).

Kasper, D. et al., Protective Efficacy of Immunization with Capsular Antigen against Experimental Infection with *Bacteroides fragilis*; J. of Infectious Diseases 140:724–731 (1979).

(List continued on next page.)

*Primary Examiner*—John Kight
*Assistant Examiner*—Howard C. Lee
*Attorney, Agent, or Firm*—Wolf, Greenfield & Sacks, P.C.

[57] ABSTRACT

Methods and products for protecting against abscess formation associated with surgery, trauma or diseases that predispose the host to abscess formation are provided. Methods for forming immunomodulators and pharmaceutical compositions relating thereto also are provided. The products useful in the invention are polysaccharides including a repeat unit having a positively charged free amino group and a negatively charged group. The preferred polysaccharide is *B. fragilis* capsular polysaccharide A.

31 Claims, No Drawings

OTHER PUBLICATIONS

Kenne, L. et al., Structural Studies of the O-Specific Side-Chains of the *Shigella sonnei* Phase I Lipopolysaccharide; Carbohydrate Res., 78:119–126, (1980).

Knirel, Y.A. et al., Somatic Antigens of *Pseudomonas aeruginosa*; European J. of Biochemistry, 167:549–561 (1987).

Knirel, Y.A. et al., The Structure of O-Specific Polysaccharides and Serological Classification of *Pseudomonas aeruginosa*; Acta Microbiologica Hungarica 35:3–24 (1988).

Lindberg, B. et al., Structural Studies of the Capsular Polysaccharide from *Streptococcus pneumoniae* Type 1; Carbohydrate Res 78:111–117 (1980).

Onderdonk, A. et al., Evidence for T Cell-dependent Immunity to *Bacteroides fragilis* in an Intraabdominal Abscess Model; J. Clin Invest. 69:9–16 (1982).

Onderdonk, A. et al., The Capsular Polysaccharide of *Bacteroides fragilis* as a Virulence Factor: Comparison of the Pathogenic Potential of Encapsulated and Unencapsulated Strains; J. Infect. Diseases 136:82–89 (1977).

Paloeleti et al., Effects of Chain Length on the Immunogenicity of Rabbits of Group B Streptococcus Type III Oligosaccharide-Tetanus Toxoid Conjugates; J. Clin. Invest. 89:203–209 (1992).

Pantosti et al., Immunochemical Characterization of Two Surface Polysaccharides of *Bacteroides fragilis*; Infection and Immunity 59:2075–2082 (1991).

Pantosti et al., *Bacteroides fragilis* Strains Express Multiple Capsular Polysaccharides; J. Clin. Microbiol. 31(7):1850 (1993).

Reed, L. et al., A Simple Method of Estimating Fifty Percent Endpoints; Am. J. Hyg. 27:493 (1938).

Shapiro, M. et al, Cellular Control of Abscess Formation: Role of T Cells in the Regulation of Abscesses Formed in Reponse to *Bacteroides fragilis*; J. Immunol., 137:341–346 (1986).

Shapiro, M. et al., Cellular Immunity to *Bacteroides fragilis* Capsular Polysaccharide; J. Exp. Med. 154:1188–1197 (1982).

Szu, S.C. et al., Relation Between Structure and Immunologic Properties of the Vi Capsular Polysaccharide; Infection and Imm. 59:4555–4561 (1991).

Taylor, RL. et al., Stoichimetric Depolymerization of Polyuronides and Glycosaminoglycuronans to Monsaccharides following Reduction of their Carbodiimide-Activated Caroxyl Groups; Biochem. 11:1383 (1972).

Tzianabos, A. et al., Abstract, The Am. Society for Microbiology (94th General Mtng.) B–206, May 23–27 (1994).

Tzianabos, A. et al., Abstract, the International Carbohydrate Symposium XVIII, Jul. 21, 1994.

Tzianabos, A. et al., Structural Features of Polysaccharides that Induce Intra-Abdominal Abscesses; Science 262:416–419(1993).

Tzianabos, A. et al., The Capsular Polysaccharide of *Bacteroides fragilis* Comprises Two Ionically Linked Polysaccharides; J.Biol. Chem. 267:18230–18235 (1992).

Wessels, M.R. et al., Structure and Immunochemistry of an Oligosaccharide Repeating Unit of the Capsular Polysaccharide of Type III Group B Streptococcus; J. Biol. Chem. 262:8262–8267 (1987).

Zaleznik, D. et al., A Soluble Suppressor T Cell Factor Protects Against Experimental Intraabdominal Abscesses; J. Clin. Invest. 75:1023–1027 (1985).

Tzianabos, A. et al., Structural Characteristics of Polysaccharides That Induce Protection against Intra-Abdominal Abcess Formation; Infection and Immunity 62:4881–4886 (1994).

Jennings et al. *The Journal of Immunology*, vol. 137: 1708–1713, (1986).

Jotwani et al. *Microbiol. Immunol.*, vol. 36: 1041–1049, (1992) Abstract only.

Meisel-Mikolajczyk et al., *Archivum Immunologiae et Therapie Experimentalis*, vol. 41, pp. 129–131, (1993) abstract only.

The Merck Index (Eleventh Edition), pp. 734–735, (1989).

5,679,654

CAPSULAR POLYSACCHARIDE IMMUNOMODULATOR

This invention was made with government support from NIH R01 A1 22807, F32 A1 084901. The government has certain rights to this invention.

FIELD OF THE INVENTION

This invention relates to immunomodulators and methods for protecting a subject against abscess formation associated with bacterial infection or contamination.

BACKGROUND

A commonly occurring complication associated with leakage of colonic bacteria into the peritoneum is intra-abdominal sepsis and abscess formation. An abscess is an encapsulated collection of bacteria, lymphocytes, macrophages, polymorphonuclear leukocytes and fibrin that forms in response to bacterial insult or contamination within the peritoneal cavity, such as occurs during a surgical procedure, trauma or diseases Such as appendicitis or cancer. Invasion of the exposed body area by the bacteria may occur in a localized area within the peritoneal cavity, retroperitoneal space, pelvis or other spaces or organs in the body. The infected tissue area remains relatively immune to antibiotics which are unable to penetrate the tissue structures and effectively clear walled-off bacteria. If the abscess is left untreated, it may cause fever, prolonged hospitalization, and in some cases mortality. If the abscess ruptures, it will release its bacterial contents into the peritoneal cavity, which can in turn lead to recurring sepsis in these patients. Currently when abdominal surgeries are performed, antibiotics are administered prophylactically as well as post-operatively. However, once an abscess has formed, the major course of action is further surgical intervention to drain the offending abscess. The result is a time-consuming and costly procedure, running on the average of $10,000 per patient.

It has been impractical to immunize patients against abscess formation such as in the case of intraabdominal surgery. This traditional approach to treatment or prevention is not possible because there simply are too many strains of bacteria capable of causing abscess formation, and protection against one would not confer protection against another. It furthermore is unsettled whether vaccination and consequent induction of an immune response would confer adequate protection against abscess formation by any particular bacterium. There also exist problems and dangers associated with administering live or attenuated strains of bacteria to humans, further discouraging efforts to produce vaccines containing a large number of different bacteria.

Capsular polysaccharides of bacteria can be found covering the surface of some bacteria pathogenic to humans. Polysaccharides have been characterized as T-cell independent antigens that elicit humoral antibody responses. Although many polysaccharides have been shown to be immunogenic, some are only weakly immunogenic at best.

*Bacteroides fragilis* is a predominant obligate anaerobe isolated from intra-abdominal abscesses. The capsular polysaccharide complex (CPC) has been identified as the region of *B. fragilis* which causes abscess formation. This carbohydrate complex covers the surface of *B. fragilis*. This isolated complex alone can interact with the host immune system to elicit a patho-biologic response that results in fully formed abscesses in individuals injected with the complex. Studies were performed in rodent models in which *B. fragilis* or its CPC were injected intraperitoneally. Both intact *B. fragilis* and CPC alone provoked abscess formation associated with intra-abdominal sepsis.

It was investigated whether the CPC of *B. fragilis* could be used to immunize subjects against subsequent infection and abscess formation by *B. fragilis*. It was by no means predictable that this would be possible based upon the ability of CPC alone to provoke abscess formation because "immunity" and abscess formation are not known to result from remotely related immunological responses. When CPC was administered subcutaneously it was found to confer immunological protection against abscess induction in a rat model. Protection against abscess formation by this polysaccharide complex was determined to be mediated by a T cell-dependent host response. Prior to this finding, bacterial polysaccharides have been classified as T cell-independent antigens that only elicit humoral responses.

Although subcutaneous administration of either *B. fragilis* or CPC is sufficient to protect animals against abscess formation subsequent to challenge with *B. fragilis* or CPC, neither conferred immunity against other bacterial strains, as was expected. They therefore have no use as a "vaccine" for bacterial infection caused by the multitude of organisms normally found in the colon.

The CPC consists of two distinct high molecular weight polysaccharides, termed A and B. Each polysaccharide is composed of distinct oligosaccharide repeating units possessing uncommon constituent sugars with free amino, carboxyl and phosphonate groups. Polysaccharide A has a tetrasaccharide repeating unit with a balanced positively charged amino group and negatively charged carboxyl group. Polysaccharide B has a hexasaccharide repeating unit, including an unusual 2-amino ethylphosphonate substituent containing a free amino group and negatively charged phosphate group. The galacturonic acid residue contains an additional negatively charged carboxyl group. Ionic interaction between the two saccharide chains tightly links polysaccharides A and B into a high molecular weight complex. The complex capsular motif is a conserved trait for all strains of *B. fragilis* that have thus far been examined.

It would be extremely desirable to have a pharmaceutical preparation that could protect a host organism against abscess formation associated with infection by multiple bacterial strains.

SUMMARY OF THE INVENTION

Methods and products for protecting against abscess formation associated with surgery, trauma or diseases that predispose the host to abscess formation are provided. Methods for forming immunomodulators and pharmaceutical compositions relating thereto also are provided.

It has been discovered that polysaccharides having a particular structural motif can protect animals against challenge with abscess-inducing bacteria. This motif includes possession of a positively charged free amino group and a negatively charged group on a polysaccharide repeating unit. Such polysaccharides are capable of inducing "cross-protection". That is, a single polysaccharide can produce protection against abscess formation by a variety of bacteria.

According to one aspect of the invention, a method for inducing protection against abscess formation associated with surgery, trauma or diseases that predispose the host to abscess formation is provided. A pharmaceutical preparation is administered to a subject in conjunction with intra-abdominal surgery or upon presentation of a predisposing condition. The preparation includes an effective amount for inducing protection against abscess formation of a polysaccharide formed of repeating units of a maximum of ten saccharides, wherein each repeating unit includes at least one free amino moiety and one negatively charged moiety selected from the group consisting of carboxyl, phosphate and phosphonate, and wherein the polysaccharide is free from dimerization as part of a *B. fragilis* capsular polysaccharide complex. Preferably the polysaccharide is formed of repeating units of a maximum of five monosaccharides. Such polysaccharides occur in nature and may be isolated. One such polysaccharide, the most preferred, is a capsular polysaccharide A of the *B. fragilis* capsular polysaccharide complex. In nature the polysaccharide A occurs only in dimerized form, tightly bound to the *B. fragilis* capsular polysaccharide B as a dimer, the A:B capsular polysaccharide complex is not capable of inducing cross-protection to infection with other bacteria. Thus, the invention contemplates administration of isolated capsular polysaccharide A, free from dimerization as part of a *B. fragilis* capsular polysaccharide complex.

The polysaccharides useful according to the invention also may be synthesized from naturally occurring polysaccharides that do not possess the requisite motif. For example, certain naturally occurring polysaccharides have a negatively charged group and at least one N-acetyl moiety on each repeating unit. Such polysaccharides may be de-N-acetylated to convert the N-acetyl moiety to a free amino moiety, thereby creating the necessary structural motif for use according to the invention. Other naturally occurring polysaccharides include imine groups which can be reduced to form a free amino moiety, thereby creating together with a negatively charged group the structural motif necessary for usefulness according to the invention.

Thus, the invention contemplates methods for preparing pharmaceuticals by selecting polysaccharides having repeating units of a maximum of ten saccharides, each unit having at least one negatively charged moiety selected from the group consisting of carboxyl, phosphate and phosphonate. Each repeating unit also includes a moiety that may be modified to form a free amino moiety. Such modified polysaccharides then are mixed with pharmaceutically acceptable carriers, preferably in amounts to form effective doses for protecting a subject against abscess formation associated with surgery, trauma or diseases that predispose the host to abscess formation.

Pharmaceutical preparations also are provided. The pharmaceutical preparations include a polysaccharide formed of repeating units of a maximum of ten saccharides, each repeating unit including a free amino moiety and a negatively charged moiety selected from the group consisting of carboxyl, phosphate and phosphonate, together with a pharmaceutically acceptable carrier. The polysaccharide is free from dimerization as part of a *B. fragilis* polysaccharide complex. Preferably the polysaccharide is a bacterial polysaccharide and most preferably the polysaccharide is a component of the *B. fragilis* capsular polysaccharide complex. The capsular polysaccharide A may also be modified to contain a hydroxymethyl group.

Exemplary pharmaceutical preparations include monomers that carry both the free amino group and the negatively charged group, dimers in a 1–4 linkage wherein the negatively charged group is on the first saccharide and trimers wherein the negatively charged group is on the first saccharide, wherein the free amino moiety is also on the first saccharide and/or wherein the third saccharide is free of any amino or negatively charged moiety. The most preferred preparation is a polysaccharide that has a repeating unit of a tetramer with a trimeric backbone, characteristic of *B. fragilis* capsular polysaccharide A.

According to another aspect of the invention, the products and methods of the invention are administered together with cytokines and/or antibiotics, which may form a part of the pharmaceutical preparations of the invention. Preferred cytokines are those that enhance a subject's T cell response. Such cytokines include those that activate both T and B cells, but cytokines that enhance the T cell response exclusive of B cell enhancement are preferred. Thus, the invention involves pharmaceutical preparations containing such cytokines together with any polysaccharide useful according to the invention and as described above. This includes naturally occurring bacterial polysaccharides that previously may have been used as immunogens to stimulate a humoral B cell response, but have not before been used to protect against abscess formation and have not been used together with cytokines that enhance a T cell response (e.g. *Streptococcus pneumoniae* polysaccharide, *Trypanosoma cruzi* lipopeptidophosphoglycan and *Pseudomonas aeruginosa* Fisher immunotype, 7 O-antigen).

The bacterial polysaccharides of the invention most likely act to stimulate T-cell proliferation, which has not before been described in connection with bacterial polysaccharides. The invention avoids the dangers associated with using live bacteria to stimulate an immune response and further provides cross-protection against a variety of strains of bacteria. The invention further can be used in connection with both planned and emergency surgeries, trauma or diseases that predispose the host to abscess formation.

These and other aspects of the invention are described in greater detail below.

DETAILED DESCRIPTION OF THE INVENTION

The invention is useful whenever it is desirable to prevent bacterial abscess formation in a subject. This includes prophylactic treatment to prevent such conditions in planned surgical procedures as well as emergency situations. Elective surgeries include the following intra-abdominal surgeries: right hemicolectomy; left hemicolectomy; sigmoid colectomy; subtotal colectomy; total colectomy; laparoscopic or open cholecystectomy (gall bladder); gastrectomy; etc. Emergency surgeries include those to correct the following conditions: perforated ulcer (duodenal or gastric); perforated diverticulitis; obstructive diverticulitis; perforated appendicitis; blunt abdominal trauma; penetrating abdominal trauma; etc. The invention also is useful with nonintra-abdominal surgeries such as cardiac surgeries and surgeries to correct wound infections. The invention also is useful in connection with diseases that predispose a subject to abscess formation such as pelvic inflammatory disease, urinary tract infections and colon cancer. Those of ordinary skill in the art to which this invention pertains will recognize the range of conditions and procedures with which the invention is useful. A subject as used herein means: humans, primates, horses, cows, sheep, pigs, goats, dogs, cats, and rodents.

It has been discovered that certain polysaccharides can be used to stimulate host T-cells and induce protection against numerous bacteria. This protective effect is T-cell dependent and not mediated by a humoral antibody response. As such, administration of the preparations of the invention is not "vaccination" and the preparations are not "vaccines" which mediate protection that is specific to bacteria expressing the immunizing antigen.

It was discovered that the *B. fragilis* capsular polysaccharide A (PSA), when separated from the polysaccharide A:B dimer complex, was capable of conferring protection against abscess formation resulting from challenge with *B. fragilis* and other bacterial species. This was unexpected because PSA does not exist and it was not predictable that PSA would have any activity when separated from PSB. What is more surprising is that this protection extends to abscess formation resulting from infection by organisms other than *B. fragilis* because PSA does not exist on bacteria other than *B. fragilis*. Thus, the preparations of the invention represent the first "universal" immunomodulators capable of protecting against abscess formation that might result from infection/contamination by any number of bacteria. The invention thereby opens the door to pretreating abdominal surgical patients, trauma patients or patients with diseases that predispose the host to abscess formation with a safe immunomodulator to provoke a generalized immune response to protect against abscess formation.

The protective effect described above was seen also using B. fragilis polysaccharide B (PSB), isolated and separated from polysaccharide A.

PSA has the following structure:

It was determined that there are particular structural features on polysaccharide A and B which mediate its ability to induce intra-abdominal abscesses. Chemical neutralization or removal of the charged amino or carboxyl group abrogated abscess induction by these polysaccharides. Polysaccharides from other organisms, such as the group antigen or capsular polysaccharide from *Streptococcus pneumoniae* type 1 strains, that had different repeating unit structures but the same charged structural groups (i.e., at least one free amino and one negatively charged group) also promoted abscess formation. Both the positively and negatively charged groups on these polysaccharides also modulate their ability to induce abscess formation and to protect

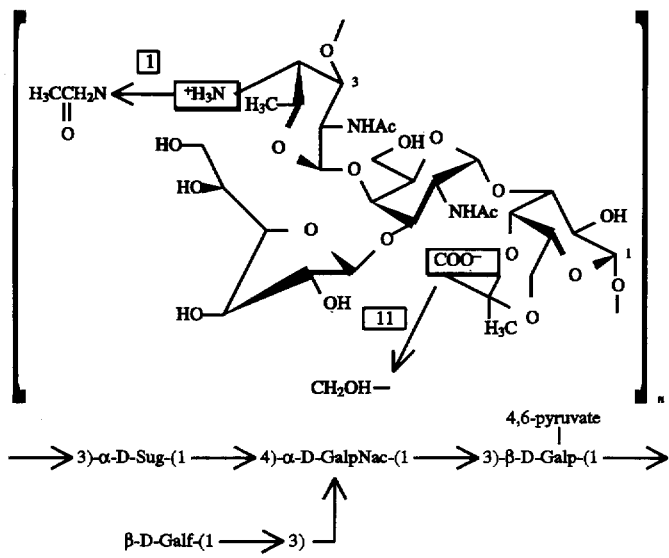

PBS has the following structure:

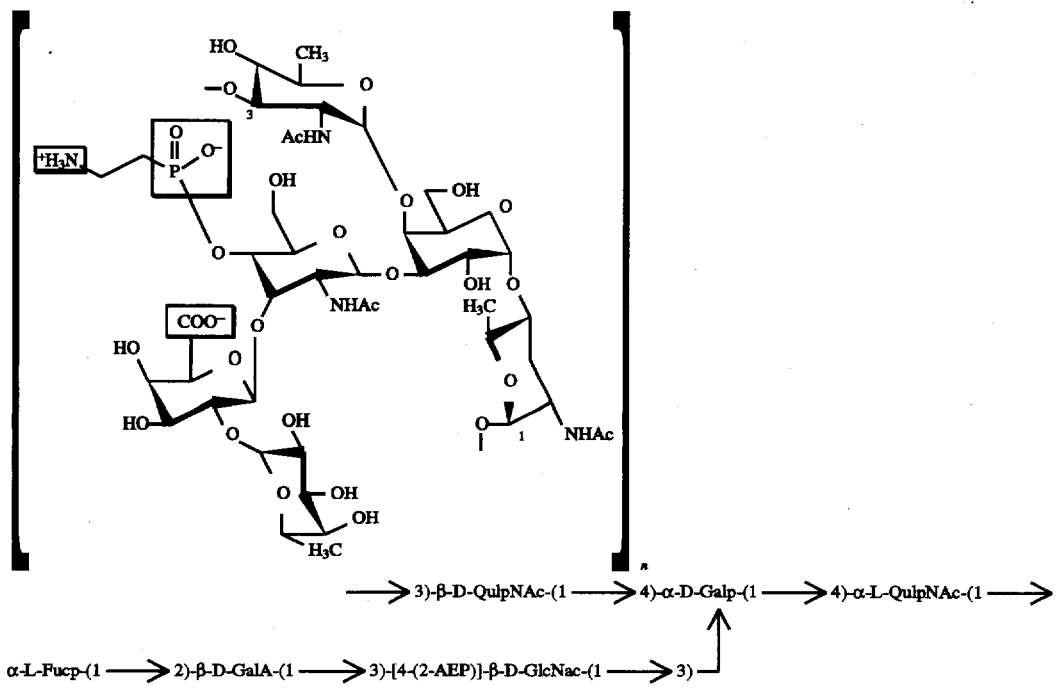

animals against abscess formation. Immunization with either polysaccharide A or B protected animals against abscess formation subsequent to challenge with polysaccharide A, B or *S. pneumoniae* type 1 capsular polysaccharide. Both the positive and negative charges on polysaccharide A are essential to the ability of this polymer to confer protection against abscess formation, as neutralization of either charge abrogated the protection. The ability of polysaccharide A or B to confer protection against abscess formation is mediated by T cells.

Polysaccharides useful according to the present invention include those naturally occurring polysaccharides that include the requisite charged groups. These polysaccharides may be derived from bacterial sources. Bacteria used as starting materials to obtain capsular polysaccharides can be obtained commercially from a number of sources. For example, the *B. fragilis*, NCTC 9343 and ATCC 23745 may be obtained from the National Collection of Type Cultures (London, England) and the American Type Culture Collection (Bethesda, Md.). Polysaccharide A and polysaccharide B can be purified from the above bacteria following the protocol of Pantosti et al. *Infection and Immunity* 59:2075–2082 (1991), the details of which are described briefly in Example 1.

In addition to the naturally occurring polysaccharides, polysaccharide repeating units that consist of at least one N-acetyl sugar and at least one uronic acid (sugar with a negatively charged carboxyl group) can be modified to produce the immune response of the present invention. A polysaccharide repeating unit containing at least one N-acetyl sugar and at least one uronic acid can be de-N-acetylated to create a free amino group and thus will yield a polysaccharide with the correct charge motif. Molecules which may be de-N-acetylated include *Salmonella typhi* capsular polysaccharide (VI antigen), *Escherichia coli* K5 capsular polysaccharide, *Staphylococcus aureus* type 5 capsular polysaccharide, Group B Streptococcus type III capsular polysaccharide, and *Rhizobium meliloti* exopolysaccharide II (all described in greater detail below).

Bacterial polysaccharides which possess imine groups (C=NH) in addition to free carboxyl groups may be modified and used to produce the immune response of the present invention. Many of the pseudomonis aeruginosa O-specific side chains possess imine groups. Imine groups can be reduced with sodium borohydride (NaBH$_4$) to create free amino groups (NH$_3$+). An example of a compound which may be reduced with sodium borohydride to create free amino groups is *Pseudomonis aeruginosa* Fisher 7.

The most preferred polysaccharide antigen is the capsular polysaccharide A from *B. fragilis*, modified slightly. Modification of polysaccharide A by oxidation with 0.01M Sodium metaperiodate (NaIO$_4$) by the procedure of Teleti et al. *Journal of Clinical Investigation* 89:203–209 (1992) enhances the biological activity.

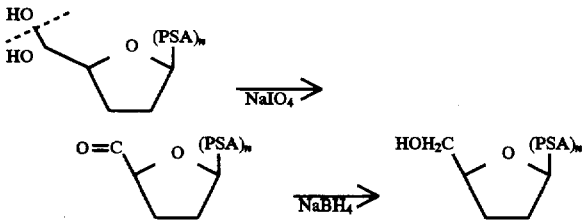

This modification selectively creates carbonyl groups (C=O) on the galactofuranose side chain of the polysaccharide A repeating unit. This group is very amenable to reduction with a reducing agent such as sodium borohydride and will convert it to a hydroxymethyl group (CH$_2$OH)(see Example 5).

The size of the polysaccharides useful according to the invention varies greatly. Polysaccharides between 500 and 20,000,000 daltons will be typical. Polysaccharide A is about 2,000,000 daltons.

The polysaccharides useful in the invention may be delivered in mixtures of more than one polysaccharide. A mixture may consist of several polysaccharides.

As discussed above, naturally occurring polysaccharides can be modified to yield immunomodulators useful in the invention. *Salmonella typhi* has a capsular polysaccharide (Vi antigen) that is formed entirely of repeating monomers of galactosaminuronic acid. This acid includes a carboxylic moiety and an N-acetyl moiety. The N-acetyl moiety can be modified to yield a free amino group such that each monomeric repeating unit then has both a positively and negatively charged group.

Polysaccharides that are dimers exist and can be modified to yield immunomodulators useful in the invention. *Esherichia coli* K5 capsular polysaccharide is formed of repeat units of a dimer of glucuronic acid and glucosamine linked together in 1–4 linkages. The glucuronic acid carries a carboxylic acid moiety and the glucosamine carries an N-acetyl group, which can be modified to form a free amino group. When so modified a dimeric repeat unit having both a negatively charged moiety (on the first sugar) and a free amino group (on the second sugar) is formed.

Polysaccharides that are trimers exist and can be modified to yield immunomodulators useful in the invention. *Staphylococcus aureus* type 5 capsular polysaccharide is formed of repeat units of a trimer of mannosaminuronic acid—fucosamine—fucosamine. The mannosaminuronic acid carries a carboxylic acid moiety and the fucosamines carry N-acetyl moities which can be modified to form free amino moieties. When so modified, a trimeric repeat unit having a negatively charged moiety (on the first sugar) and at least one positively charged moiety (on the second and third sugars) is formed. In a similar manner, *Pseudomonas aeruginosa* O-antigens can be modified to yield immunomodulators useful in the invention. Examples include trimers that carry carboxylic acid moieties and imine moieties which can be modified to yield free amino groups. Fisher immunotype 7, Lanyi-Bergan 02a, 02b and Lanyi-Bergan 02d, and 2f have polysaccharides formed of trimeric repeat units with carboxylic acid moieties on the first and second sugars and an imine moiety on the first sugar. (The third sugar is free of a charged moiety; all sugars also carry an N-acetyl moiety). For example, the first sugar can be modified so as to carry both a free amino moiety and the carboxylic acid moiety. Likewise the N-acetyl groups could be modified to yield a different arrangement useful according to the invention.

Polysaccharides that have longer repeat units such as tetramers and pentamers also can be modified as described above. It is believed that repeat units up to decimers are useful according to the invention. In addition, repeat units including side chain sugars also are useful, including those wherein one or both of the free amino and negatively charged moieties are located on such side chains. Furthermore, such side chains carrying the charged moieties need not be sugars, although it is preferred that at least the backbone of the repeat unit be made up of only sugars.

It is preferred that the repeat unit have no more than three free amino groups, and preferably no more than two such groups. It also is preferred that there be at least one negatively charged group for each free amino group.

The starting materials further need not be derived from bacterial origin. Any polysaccharides carrying carboxylic acid moieties and N-acetyl or imine groups may be modified as described above.

Specific examples together with chemical names and structural formulas are as follows. The invention, however, is by no means limited to the following examples. In the chemical formulas, use is made of the following abbreviations:

AAT=2-acetamido-4-amino-2,4,6-tridoxy-D-galactose
A=uronic acid
NAc=N-acetyl group
p=pyranose
AEP=2-aminoethylphosphonate
OAc=0-acetyl group Polysaccharides having N-acetyl moieties:

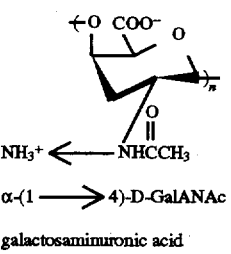

α-(1 ⟶ 4)-D-GalANAc galactosaminuronic acid

The N-acetyl group structure and its modification to a free amino group are illustrated for the above polysaccharide only. N-acetyl groups will be abbreviated as NHAc in the structural formulas of the subsequent examples.

*Esherichia coli*K5 capsular polysaccharide

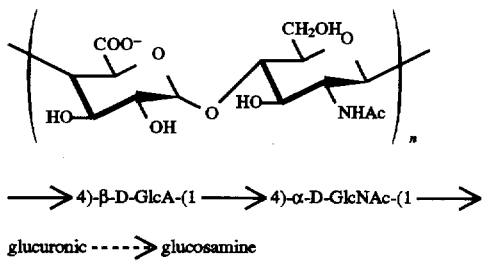

⟶ 4)-β-D-GlcA-(1 ⟶ 4)-α-D-GlcNAc-(1 ⟶ glucuronic ----⟶ glucosamine

*Staphylococcus aureus* type 5 capsular polysacharide

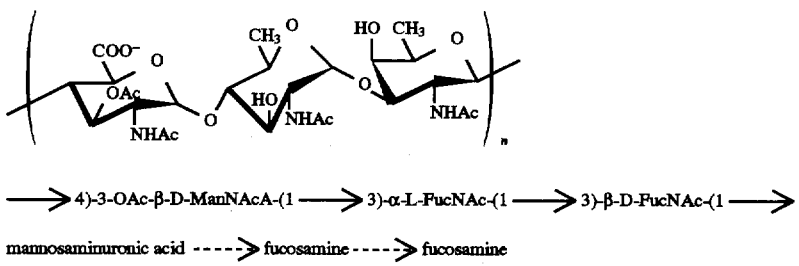

⟶ 4)-3-OAc-β-D-ManNAcA-(1 ⟶ 3)-α-L-FucNAc-(1 ⟶ 3)-β-D-FucNAc-(1 ⟶ mannosaminuronic acid ----⟶ fucosamine ----⟶ fucosamine

*Rhizobium melilori* exopolysaccharide II

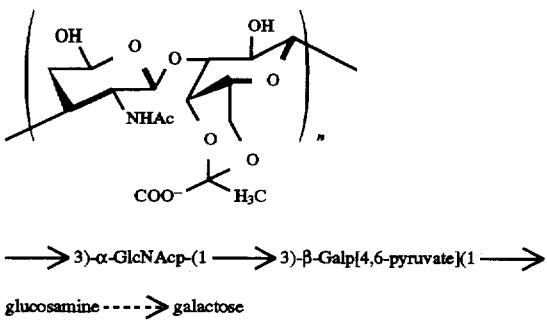

⟶ 3)-α-GlcNAcp-(1 ⟶ 3)-β-Galp[4,6-pyruvate](1 ⟶ glucosamine ----⟶ galactose group B streptococcus type III capsular polysaccharide

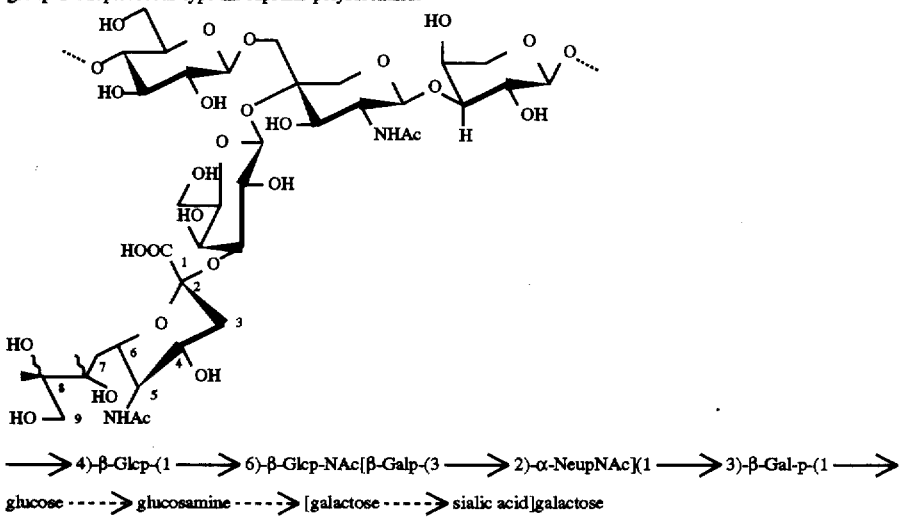

→ 4)-β-Glcp-(1 ──→ 6)-β-Glcp-NAc[β-Galp-(3 ──→ 2)-α-NeupNAc](1 ──→ 3)-β-Gal-p-(1 ──→ glucose ----> glucosamine ----> [galactose ----> sialic acid]galactose

Polysaccharide having an imine moiety:

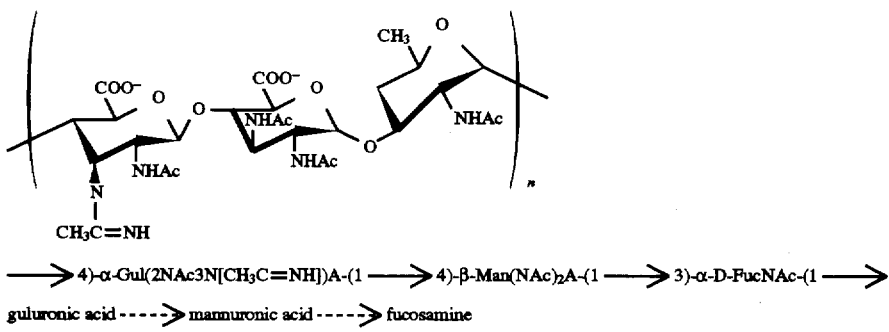

→ 4)-α-Gul(2NAc3N[CH₃C=NH])A-(1 ──→ 4)-β-Man(NAc)₂A-(1 ──→ 3)-α-D-FucNAc-(1 ──→ guluronic acid ----> mannuronic acid ----> fucosamine

De-N-acetylation can be accomplished by conventional chemistry techniques well known to those of ordinary skill in the art. One suitable method involves the use of alkali with or without sodium borohydride. Twenty mg of polysaccharide is dissolved in 2M NaOH(3 ml) and sodium borohydride is added (50 mg). The solution is heated to 100° C. for 5 h. Following neutralization with acid, the solution is dialyzed against distilled water in the cold and freeze-dried. DiFabio, J. L, Michon, F., Brisson, J. R., Jennings, H. J., Weasels, M. R. Benedi, V. J., Kasper, D. L. Structure of the capsular polysaccharide antigen of type IV groups B Streptococcus. 1989. Canadian Journal of Chemistry, 67:877–882.

For those polysaccharides that contain imine moieties (C—NH), free amino groups can be formed by conventional chemistry techniques known to those of ordinary skill in the art. One suitable method involves the use of sodium borohydride. The imine group can be reduced with sodium borohydride to create a free amino group. This is done by adding in excess of 5 mg of borohydride to polysaccharide dissolved in distilled water while stirring at room temperature for 2 hours. The mixture is then dialyzed against water and freeze dried. The reference from the reduction procedure above applies here as well.

Naturally occurring polysaccharides also may be used without modification in the methods of the invention and in forming the pharmaceutical preparations of the invention. Non-limiting examples are as follows:

*Shigella sonnei* Phase I lipopolysaccharide O-antigen

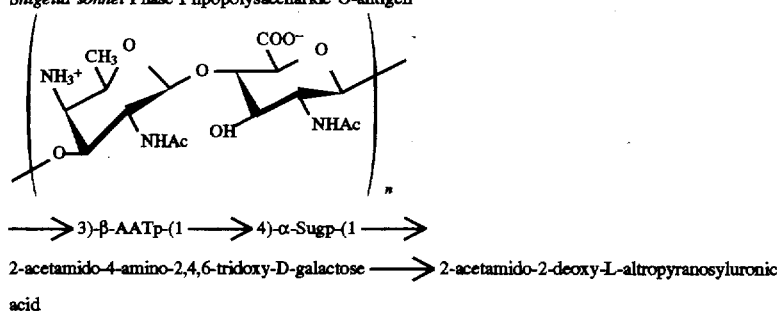

⟶ 3)-β-AATp-(1 ⟶ 4)-α-Sugp-(1 ⟶

2-acetamido-4-amino-2,4,6-tridoxy-D-galactose ⟶ 2-acetamido-2-deoxy-L-altropyranosyluronic acid

*Streptococcus pneumoniae* type 1 capsular polysaccharide

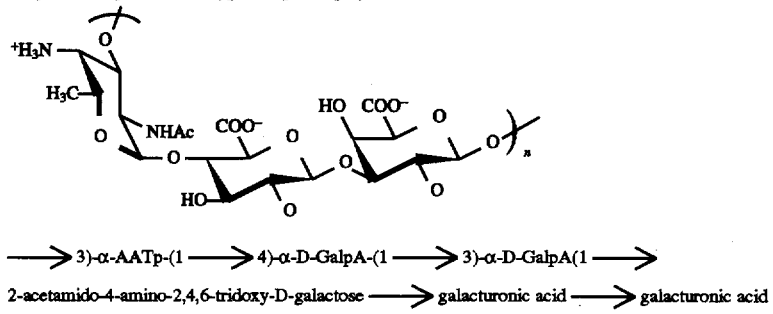

⟶ 3)-α-AATp-(1 ⟶ 4)-α-D-GalpA-(1 ⟶ 3)-α-D-GalpA(1 ⟶

2-acetamido-4-amino-2,4,6-tridoxy-D-galactose ⟶ galacturonic acid ⟶ galacturonic acid

*Streptococcus pneumoniae* group antigen: C substance

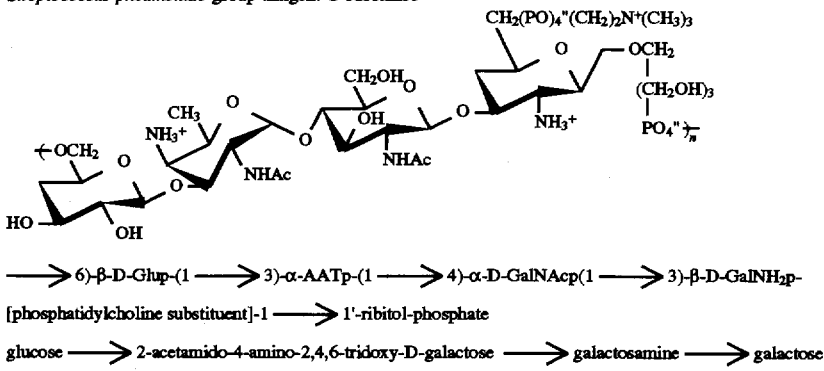

⟶ 6)-β-D-Glup-(1 ⟶ 3)-α-AATp-(1 ⟶ 4)-α-D-GalNAcp(1 ⟶ 3)-β-D-GalNH₂p-

[phosphatidylcholine substituent]-1 ⟶ 1'-ribitol-phosphate glucose ⟶ 2-acetamido-4-amino-2,4,6-tridoxy-D-galactose ⟶ galactosamine ⟶ galactose A polysaccharide that does not have solely a sugar backbone but still is believed to be useful according to the invention is *Trypanosoma cruzi* lipopeptidophosphoglycan: Galf-β-(1→3)-α-Manp(12)-α-Manp(16)[Galf]-α-,Manp](14)Glc pNH₂[2-AEP]-Inositol-phosphate-ceramide.

The naturally occurring polysaccharides that may be used without modification also may be modified to selectively add, subtract or modify various moieties, including free amino moieties, negatively charged moieties or other moieties. Examples include adding free amino moities by modifying existing N-acetyl groups or imine groups or forming hydroxymethyl groups from alcohol groups.

Polysaccharides useful according to the invention may be obtained from commercial sources or may be isolated and derived from bacteria, seaweed and the like. The following is a list of bacterial polysaccharides and references which detail the isolation and preparation of such polysaccharides.

*Salmonella typhi* capsule (Vi antigen), Szu, S. C., X. Li, A. L. Stone and J. B. Robbins, Relation between structure and immunologic properties of the Vi capsular polysaccharide, *Infection and Immunity*. 59:4555–4561 (1991).

*E. Coli* K5 capsule, Vann, W., M. A. Schmidt, B. Jann and K. Jann, The structure of the capsular polysaccharide (K5 antigen) of urinary tract infective *Escherichia coli*, 010:K5S:H4. A polymer similar to desulfo-heparin, *European Journal of Biochemistry*. 116: 359–364, (1981).

*Staphylococcus aureus* type 5 capsule, Fournier, J. -M., K. Hannon, M. Moreau, W. W. Karakawa and W. F. Vann, Isolation of type 5 capsular polysaccharide from *Staphylococcus aureus*, *Ann. Inst. Pasteur/Microbiol.* (Paris). 138: 561–567, (1987).

*Rhizobium melilori* expolysaccharide II, Glazebrook, J. and G. C. Walker, a novel expolysaccharide can function in place of the calcofluoer-binding exopolysaccharide in nodulation of alfalfa by *Rhizobium meliloti Cell.* 65:661–672 (1989).

Group B streptococcus type III, Wessels, M. R., V. Pozsgay, D. L. Kasper and H. J. Jennings, Structure and immunochemistry of an oligosaccharide repeating unit of the capsular polysaccharide of type III group *B Streptococcus*. *Journal of Biological Chemistry*. 262:8262–8267 (1987).

*Pseudomonas aeruginosa* Fisher 7 O-specific side-chain, Knirel, Y. A., N. A. Paramonov, E. V. Vinogradov, A. S.

Shashkow, B. A. N. K. Kochetkov, E. S. Stanislavsky and E. V. Kholodkova, Somatic antigens of *Pseudomonas aeruginosa* The structure of O-specific polysaccharide chains of lipopolysaccharides of *P. aeruginosa* 03(Lanyi), 025 (Wokatsch) and Fisher immunotypes 3 and 7, *European Journal of Biochemistry*. 167:549, (1987).

*Shigella sonnei* O-specific side chain, Kenne, L., B. Lindberg and K. Petersson, Structural studies of the O-specific side-chains of the *Shigella sonnei* phase I lipopolysaccharide, *Carbohydrate Research*. 78:119–126, (1980).

*S. pneumoniae* type I capsule, Lindberg, B., Lindqvist, B., Lonngren, J., Powell, D. A., Structural studies of the capsular polysaccharide from *Streptococcus pneumoniae* type 1, *Carbohydrate Research*. 78:111–117 (1980).

*Streptococcus pneumoniae* group antigen, Jennings, H. J., C. Lugowski and N. M. Young, Structure of the complex polysaccharide C-substance from *Streptococcus pneumoniae* type 1, *Biochemistry*. 19:4712–4719 (1980).

When administered, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The capsular polysaccharide antigen may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkyline metal or alkyline earth salts, such as sodium, potassium or calcium salts of the carboxylic acid group.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V). Suitable preservatives include benzalkonium chloride (0.003–0.03% W/V); chlorobutanol (0.3–0.9% W/V); parabens (0.01–0.25% W/V) and thimerosal (0.004–0.02% W/V).

The immune stimulating polysaccharide preparation of the present invention may be a pharmaceutical composition having an effective amount of a polysaccharide optionally included in a pharmaceutically-acceptable carrier. The term "pharmaceutically-acceptable carrier" as used herein, and described more fully below, means one or more compatible solid or liquid filler, dilutants or encapsulating substances which are suitable for administration to a human or other animal.

In the present invention, the term "carrier" denotes an organic or inorganic ingredient, natural or synthetic, with which the active ingredient is combined to facilitate the application. The components of the pharmaceutical compositions also are capable of being comingled with the polysaccharides of the present invention, and with each other, in a manner such that there is no interaction which would substantially impair the desired pharmaceutical efficiency.

Compositions suitable for parenteral administration conveniently comprise a sterile aqueous preparation of the polysaccharide, which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. Carrier formulations suitable for subcutaneous, intramuscular, intraperitoneal intraveneous, etc. administrations may be found in Remington's Pharmaceutical Sciences, Mack Publishing Company, Easton, Pa.

The term "adjuvant" is intended to include any substance which is incorporated into or administered simultaneously with the polysaccharide of the invention which potentiates the immune response in the subject. Adjuvants include aluminum compounds, e.g., gels, aluminum hydroxyde and aluminum phosphate, and Freund's complete or incomplete adjuvant (in which the polysaccharide antigen is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U) leutinan, pertussis toxin, lipid A, saponins and peptides, e.g. muramyl dipeptide. Rare earth salts, e.g., lanthanum and cerium, may also be used as adjuvants. The amount of adjuvants depends on the subject and the particular polysaccharide used and can be readily determined by one skilled in the art without undue experimentation. Preferred adjuvants are those that selectively stimulate T-cells. It is desirable to avoid adjuvants that might suppress a T-cell response.

Cytokines may be delivered in conjunction with the immunomodulators of the invention and "cocktails" including the immunomodulators and the cytokines are contemplated. The cytokines contemplated are those that will enhance the beneficial effects that result from administering the immunomodulators according to the invention. Cytokines are factors that support the growth and maturation of cells, including lymphocytes. Important to the invention herein is stimulating T-cells, as the methods of the invention appear to be T-cell mediated. The cytokines may act directly on T-cells or indirectly on T-cells through other cells. It is believed that the addition of cytokines will augment cytokine activity stimulated in vivo by carrying out the methods of the invention. The preferred cytokines are interleukin (IL)-1, IL-2, gamma-interferon and tumor necrosis factor $\alpha$. Other useful cytokines are believed to be IL-8, IL-12 and tumor necrosis factor-$\beta$. Other cytokines known to modulate T-cell activity in a manner likely to be useful according to the invention are colony stimulating factors and growth factors including granulocyte and/or macrophage stimulating factors (GM-CSF, G-CSF and M-CSF) and platelet derived, epidermal, transforming and fibroblast growth factors. Cytokines that enhance the immune response, and particularly the T-cell response are contemplated, in general.

The precise amounts of the foregoing cytokines used in the invention will depend upon a variety of factors, including the immunomodulator selected, the dose and dose-timing selected, the mode of administration and the nature of the surgery contemplated and the characteristics of the subject. Where local administration is carried out, it will be understood that very small amounts are required (nanograms and possibly picograms) since physiological levels of cytokines are correspondingly low. The precise amounts selected can be determined without undue experimentation, particularly since a threshold amount will be any amount which will enhance the immune response. Thus, it is believed that picogram to milligram amounts are possible, depending upon the mode of delivery, but that nanogram to microgram amounts are likely to be most useful.

It will also be appreciated by those of ordinary skill in the art that the polysaccharides of the present invention have adjuvant properties by themselves. To the extent that the polysaccharides described herein potentiate human immune responses, they can be used as adjuvants in combination with other materials.

Thus, the present invention also provides pharmaceutical compositions, for medical use, which comprise polysaccharides of the invention together with one or more pharmaceutically acceptable carriers and optionally other therapeutic ingredients.

The polysaccharides useful in the invention may be delivered in the form of anti-bacterial, antibiotic cocktails. An anti-bacterial antibiotic cocktail is a mixture of any of a polysaccharide useful with this invention with another anti-bacterial antibiotic drug and/or supplementary potentiating agent. The use of antibiotics in the treatment of bacterial infection is routine. In this embodiment, a common administration vehicle (e.g., tablet, implant, injectable solution, etc.) could contain both the polysaccharide antigen useful in this invention and the anti-bacterial antibiotic drug and/or supplementary potentiating agent.

Anti-bacterial antibiotic drugs are well known and include: penicillin G, penicillin V, amphicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cepharadine, cefadoxil, cefaclor, cefazolin, cefuroxime axetil, cefamandole, cefonicid, cefoxitin, cefotaxime, ceftizoxime, cefmenoxine, ceftriaxone, moxalactam, cefotetan, cefoperazone, ceftazidme, imipenem, clavulanate, timentin, sulbactam, meomycin, erythromycin, metronidazole, chloramphenicol, clindamycin, lincomycin, aminoglycosides, quinolones and rifampin.

The polysaccharides of the invention, when used in cocktails, are administered in therapeutically effective amounts. A therapeutically effective amount will be determined by the parameters discussed below; but, in any event, is that amount which establishes a level of antibacterial reaction effective in inhibiting the abscess formation.

The preparations of the invention are administered "in conjunction with" infection. This means close enough in time with the surgery, trauma or diseases that predispose the host to abscess formation so that a protective effect against abscess formation is obtained. The preparations may be administered long before surgery in the case of elective surgery (i.e., weeks or even months) preferably with booster administrations closer in time to (and even after) the surgery. Particularly in emergency situations, the preparations may be administered immediately before (minutes to hours) and/or after the trauma or surgery. It is important only that the preparation be administered close enough in time to the surgery so as to enhance the subjects immune response against bacterial infection/contamination, thereby increasing the chances of a successful host response and reducing the likelihood of abscess formation. Multiple administrations in the days and weeks before the surgery have been shown to be effective, as discussed in greater detail below.

The preparations of the invention are administered in effective amounts. An effective amount is that amount of a polysaccharide that will alone, or together with further doses, inhibit or prevent the formation of abscess resulting from infection by a particular bacteria. It is believed that doses ranging from 1 nanogram/kilogram to 100 milligrams/kilogram, depending upon the mode of administration, will be effective. The preferred range is believed to be between 500 nanograms and 500 micrograms/kilogram, and most preferably between 1 microgram and 100 micrograms/kilograms. The absolute amount will depend upon a variety of factors including whether the administration is in conjunction with elective surgery or emergency surgery, concurrent treatment, number of doses and individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the pharmaceutical compositions of the invention are contemplated. The invention has been shown to be effective with multiple doses administered over a three week period preceding surgery, over a two week period preceding surgery, Over a one week period preceding surgery and even when the first dose was administered only 24 hours preceding surgery. Further doses may be administered post surgery as well. Any regimen that results in an enhanced immune response to bacterial infection/contamination and subsequent abscess formation may be used, although optimum doses and dosing regimens are those would not only inhibit the development of abscess formation, but also would result in a complete protection against abscess formation by a particular or a variety of bacterial organisms. Desired time intervals for delivery of multiple doses of a particular polysaccharide can be determined by one of ordinary skill in the art employing no more than routine experimentation.

A variety of administration routes are available. The particular mode selected will depend, of course, upon the particular polysaccharide selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are parenteral routes. The term "parenteral" includes subcutaneous injections, intraveneous, intramuscular, intrasternal injection or infusion techniques.

The compositions may conveniently be presented in unit dosage form and may be prepared by any of the methods well known in the art of pharmacy. All methods include the step of bringing the active polysaccharide into association with a carrier which constitutes one or more accessory ingredients. In general, the compositions are prepared by uniformly and intimately bringing the antigen into association with a liquid carrier, a finely divided solid carrier, or both, and then, if necessary, shaping the product.

Other delivery systems can include time-release, delayed release or sustained release delivery systems. Such systems can avoid repeated administrations of the polysaccharides of the invention, increasing convenience to the subject and the physician. Many types of release delivery systems are available and known to those of ordinary skill in the art. They include polymer based systems such as polylactic and polyglycolic acid, polyanhydrides and polycaprolactone; non-polymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

In other embodiments, compositions of the invention can be used as reagents in immunoassays to detect T cell response against polysaccharide antigens such as *B. fragilis* capsular polysaccharide A and B. Immunoassays can be any of the conventional assay types.

EXAMPLES

Example 1

Bacterial Strain and Isolation of *B. fragilis* Polysaccharide

*B. fragilis* NCTC 9343 and ATCC 2375 were originally obtained from the National Collection of Type Cultures (London, England) and the American Type Culture Collection (Bethesda, Md.), stored at −80° F. in yeast broth until used, and grown anaerobically as previously described. Pantosti et al., *Infection and Immunity* 59:2075–2082 (1991). The CPC from *B. fragilis* NCTC 9343 ATCC 2375 was isolated by hot phenol/water extraction and subsequent purification of PS A and PS B performed as previously described. Tzianabos et al., *The Journal of Biological Chemistry* 267:18230–18235 (1992).

The *S. pneumoniae* type 1 capsular polysaccharide (CP) and other pneumococcal polysaccharides were obtained in pure form from the ATCC (MD).

Chemical Modification of Polysaccharides to Produce Molecules with Altered Charges The chemical modifications of the present invention have been described previously. Taylor. L and H. Conrad, *Biochem.* 11:1383 (1972) (reduction) and Baumann, A. et. al *Biochem.* 31:4081 (1992) (N-acetylation and deamination).

Example 2

Abscess Formation and Immune Response Induction in Rodents

Abscess Induction

The rat model of intra-abdominal sepsis used in this study has been described previously. Onderdonk, A. et. al. *J. Infect. Diseases* 136:82–89 (1977) and Tzianabos, A. et. al. *Science* 262:416–419 (1993). Briefly, male Wistar rats weighing between 180 and 200 g were selected for the experiment. Animals were housed separately and received chow (Ralston Purina, St. Louis, Mo.) and water at libitum. Animals were anesthetized with a single intraperitoneal injection of 0.15 ml of Nembutal (50 mg/ml; Abbott Laboratories, North Chicago, Ill.), and their abdomens were shaved and swabbed with a Tincture of iodine. An anterior midline incision (1 cm) was made through the abdominal wall and peritoneum, and a gelatin capsule containing 0.5 ml of innoculum was inserted into the pelvis. The incisions were closed with interrupted 3.0 silk sutures, and the animals were returned to the cages. Alternatively, in some experiments animals were directly injected with polysaccharide. The innoculum contained a 1:1 mixture of the test polysaccharide and an adjuvant solution containing sterile rat cecal contents and 10% barium sulfate (W/V). Six days later animals were necropsied in a blinded fashion and examined for the formation of one or more intra-abdominal abscesses by an observer blinded to the experimental groups. Rats were administered 10-fold dilutions of each polysaccharide. A mathematical model was used to compare the biologic activities of modified and unmodified polysaccharides over a range of three doses (200, 20 and 2 µg), and to calculate a dose of each polysaccharide that induced abscesses in 50% of the animals (AD50). Reed, L. and H. Muench, *Am. J. Hyg.* 27:493 (1938). Abscesses induced by these polysaccharides were generally uniform in size and those rats that possessed one or more fully formed abscesses were scored as positive. Animals that did not have any fully formed abscesses were scored as negative. Two control groups were included in all experiments: positive controls were challenged with intact *B. fragilis* mixed with adjuvant solution, while negative controls received adjuvant solution alone. In all cases, 100% of the positive control group and none of the negative control group developed abscesses. Data were accumulated from two separate trials.

Different polysaccharides were compared for abscess forming ability in several experiments. In Table 1 native polysaccharide A was compared with polysaccharide B and the CPC. Polysaccharide A was an order of magnitude more active ($AD_{50}$=0.67 µg) than polysaccharide B ($AD_{50}$=25 µg) or the CPC ($AD_{50}$=22 µg).

TABLE 1

| Polysaccharide | Fraction of rats with abscesses at a dose of | | | | | $AD_{50}$ (µg) | P |
|---|---|---|---|---|---|---|---|
|  | 200 µg | 20 µg | 2 µg | 0.2 µg | 0.02 µg |  |  |
| A (native) | 31/38 | 18/25 | 21/38 | 7/18 | 2/19 | 0.67 | — |
| B | 23/29 | 14/30 | 5/28 | ND | ND | 25 | — |
| CPC | 23/28 | 10/19 | 6/20 | ND | ND | 22 | — |

In Table 2 the abscess forming ability of native polysaccharides A and B were compared with chemically modified versions of polysaccharides A and B.

TABLE 2

Abscess Induction by Unmodified and Modified PS B from *B. fragilis*.

| Type of PS | Fraction of rats with abscesses at indicated dose | | | $AD_{50}$ (µg) | P value* |
|---|---|---|---|---|---|
|  | 200 (µg) | 20 (µg) | 2 (µg) |  |  |
| B (Native) | 18/19 | 13/18 | 7/19 | 4 | — |
| B (Reduced) (Modification I) | 17/18 | 15/20 | 9/19 | 3 | NS |
| B (N-acetylated) (Modification II) | 4/20 | 5/20 | 1/20 | >200 | <0.005 |
| B (De-N-acetylated) (Modification III) | 9/20 | 2/20 | 1/20 | >200 | <0.005 |
| A (native) | 16/20 | 14/20 | 10/19 | 1.3 | — |
| A (reduced) | 5/20 | 2/19 | 2/19 | >200 | <0.0005 |
| A (N-acetylated) | 7/20 | 3/19 | 1/17 | >200 | <0.0005 |
| A (deaminated) | 7/20 | 6/18 | 3/19 | >200 | <0.0005 |

*As compared with polysaccharide A or B (native).

The $AD_{50}$ of unmodified *B. fragilis* polysaccharide A was less than 2 µg (Table 2). Conversion of the negatively charged carboxyl group associated with the pyruvate substituent to a neutral hydroxymethyl group by carbodiimide reduction (reduced) created a polysaccharide with no negative charge. This modification resulted in an increase in $AD_{50}$ to greater than 200 µg. N-acetylation of the free amino group on the trideoxyfucosamine (N-acetylated) and removal of the same free amino group by nitrous deamination (deaminated) created a polysaccharide with one negative charge and no positive charges. These modifications also significantly reduced the abscess induction by these polymers so that they displayed an $AD_{50}$ of greater than 200 µg. Modification of the charged groups reduced the biologic potency by at least two orders of magnitude suggesting that polysaccharide A requires both amino (positive) and carboxyl (negative) groups to promote abscess induction in this animal model. Each of the modifications yielded a significant reduction in abscess inducing ability as compared with that of unmodified polysaccharide A (P is less than 0.0005).

The $AD_{50}$ of unmodified B. fragilis polysaccharide B was 4 µg (Table 2). Conversion of the negatively charged carboxyl group on the galacturonic acid of the polysaccharide B to a hydroxymethyl group via carbodiimide reduction (reduced) created a polysaccharide with one free amino group and one phosphonate group per repeating unit (a positive to negative charge ratio of 1:1). This modification did not alter the ability of polysaccharide B to induce abscesses as can be evidenced by the $AD_{50}$ value of 3 µg. N-acetylation of the free amino group associated with the 2-aminoethylphosphonate substituent (N-acetylated) created a polysaccharide with two negatively charged groups (carboxyl and phosphonate) and no positive charges. This modification of the free amino group to a secondary amine significantly reduced the abscess induction by this polymer so that it displayed an $AD_{50}$ of greater than 200 µg. Modification of the positive group reduced the biologic potency by at least two orders of magnitude suggesting that polysaccharide B requires at least one positive group to promote abscess induction in this animal model but that two negative groups are not required.

Replacement of acetyl groups from the three amino sugars present in the repeating unit with three free amino groups created a net positive charge on polysaccharide B with a 4:2 ratio of positively to negatively charged groups (De-N-acetylated). The de-N-acetylation of polysaccharide B significantly reduced the abscess forming potential of this saccharide ($AD_{50}$ greater than 200 µg). This result indicated that increasing the density of the charged amino groups on this polysaccharide is necessary but not sufficient to confer this biological activity. It is apparent that the density of these charged groups per repeating unit may be another critical variable regulating the ability of these polysaccharides to induce abscesses. Perhaps the increased number of positively charged amino groups on this polysaccharide prevents critical interactions with cell receptors (possibly present on T cells) that initiate the cascade of cellular events resulting in abscess formation.

Some other naturally existing and chemically modified polysaccharides were also assessed for abscess forming ability. The results of these experiments are depicted in Table 3.

TABLE 3

| Polysaccharide | Fraction of rats with abscesses at a dose of | | | $AD_{50}$ (µg) | P |
|---|---|---|---|---|---|
| | 200 µg | 20 µg | 2 µg | | |
| C substance | 17/18 | 12/18 | 6/19 | 5 | — |
| C substance (N-acetylated) | 5/10 | 1/10 | 1/10 | 200 | <0.05* |
| S. pneumoniae type 1 | 17/20 | 7/18 | 2/18 | 31 | — |
| S. pneumoniae type 1 (N-acetylated) | 6/19 | 6/20 | 3/20 | >200 | 0.018* |
| S. pneumoniae type 3 | 0/14 | 2/10 | 1/9 | >200 | <0.005* |
| Group B meningoccal | 1/10 | ND | ND | — | — |
| Group B streptococcal type Ia | 0/10 | ND | ND | — | — |
| Group B streptococcal type III | 1/10 | ND | ND | — | — |
| S. pneumoniae type 14 | 2/10 | ND | ND | — | — |
| Vi antigen | 3/20 | ND | ND | — | — |
| Vi antigen (de-N-acetylated) | 15/20 | 9/18 | 7/20 | 16 | <0.005+ |

The naturally occurring polysaccharides which have oppositely charged groups include, C substance, the group polysaccharide from Streptococcus pneumoniae, and the capsular polysaccharide of S. pneumoniae strains. C substance has a tetrasaccharide repeating unit with a total of three positive charges (conferred by a phosphatidylcholine substituent and two free amino groups) and two negative charges (conferred by phosphate groups). The capsule of S. Pneumoniae type 1 has a trisaccharide repeating unit with one positive charge (free amino group) and two negative charges (carboxyl groups). Each was a potent inducer of abscesses, with $AD_{50}$ values of 5 and 31 µg respectively. However, when each molecule was N-acetylated to neutralize the free amino group the result was a marked reduction in abscess inducing activity. This result was expected for the capsule of S. Pneumoniae type 1 based on the results obtained in Table 2. However, it was unexpected that C substance would exhibit such a dramatic reduction in activity because it still has a positive charge (conferred by a phosphatidylcholine substituent) and two negative charges. This result indicated that free amino groups on these polysaccharides are necessary for abscess-inducing activity. A different type of positive charge could not be substituted. No structural requirement exists, however, for a negatively charged group on these polymers.

Naturally occurring bacterial polysaccharides that have repeating unit structures devoid of charged groups or that have one negatively charged group per repeating unit were tested for ability to form abscesses and the results are shown in Table 3. The capsular polysaccharide of S. pneumoniae type 14 is a disaccharide repeating unit with no charged groups at all. The capsular polysaccharide of S. pneumoniae type 3, capsular polysaccharides of group B Neisseria meningitidis or of types Ia and III of group B streptococci all have one negative charge per repeating unit. Each of the above polysaccharides is a poor inducer of abscesses.

Finally, in order to determine whether an inactive polysaccharide which naturally has only a negative charge could be activated, a positive charge was added to the Vi antigen (a homopolymer of galactaminuronic acid from Salmonella typhi). Vi antigen, which has an N-acetyl group at the C-2 position of the pyranose ring and a negatively charged carboxyl group at the C-6 position, was modified by alkali treatment to produce a positively charged free amino group and a negatively charged carboxyl group. This chemical modification transformed the antigen into an abscess inducing polysaccharide.

The data presented in Tables 1–3 reveal that abscess induction in the peritoneal cavity of rodents is mediated by oppositely charges groups on bacterial polysaccharides and that a positive amino group is required.

Immune Response

Animals were vaccinated with bacterial polysaccharides by subcutaneous injection of 10 μg of polysaccharide in 0.1 ml of PBS three times a week for three weeks. Animals received a booster injection on week five and were available for challenge on week six.

The immune response conferring protection against abscess induction was measured after challenge of previously vaccinated animal with homologous and heterologous B. fragilis species as well as other homologous and heterologous bacterial polysaccharides. The results are shown in Table 4. Previous studies have shown that the 9343 CPC and 23745 CPC are distinct polysaccharide complexes. Pantosti, A. et. al., Infect. & Immun. 59:2075–2082 (1991). Immunochemical studies have demonstrated that like 9343 CPC, the 23745 CPC consists of at least two distinct polysaccharides possessing positively and negatively charged groups, although the constituent monosaccharides of the CPC found on the two strains are distinct. Pantosti, A. et. al., Infect. & Immun. 59:2075–2082 (1991) and Kasper, D. et. al., J. Bacter. 153:991–997 (1983). Heterologous and homologous B. fragilis species were used to challenge rats previously vaccinated with either purified 9343 CPC or 23745 CPC. In both cases, vaccination with CPC protected rats against abscess formation following challenge with either B. fragilis 9343 or 23745.

TABLE 4

Polysaccharide-mediated cross-protection against abscess formation by B. fragilis polysaccharides.

| Polysaccharide Vaccine (10 μg) | Challenge Polysaccharide (200 μg) | Number of rats with abscesses/total | P value* |
|---|---|---|---|
| saline | PS A | 8/8 | — |
| saline | PS B | 9/9 | — |
| saline | S. pneumoniae type 1 PS | 8/9 | — |
| saline | 9343 | 4/4 | — |
| saline | 23745 | 3/3 | — |
| PS A | PS A | 3/10 | <0.005 |
| PS A | PS B | 1/10 | <0.005 |
| PS A | S. pneumoniae type 1 PS | 3/10 | <0.05 |
| PS B | PS A | 1/8 | <0.005 |
| PS B | PS B | 2/10 | <0.005 |
| PS B | S. pneumoniae type 1 PS | 4/10 | <0.05 |
| S. pneumoniae type 1 CP | PS A | 2/10 | <0.005 |
| S. pneumoniae type 1 CP | PS B | 2/10 | <0.005 |
| S. pneumoniae type 1 CP | S. pneumoniae type 1 PS | 0/10 | <0.005 |
| 9343 CPC | 9343 | 1/10 | |
| 9343 CPC | 23745 | 1/10 | |
| 23745 CPC | 9343 | 1/10 | |
| 23745 CPC | 23745 | 1/10 | |

As described above it has been established that particular structural features (free amino and negatively charged groups) on polysaccharides mediate abscess formation. To test whether these polysaccharides confer protection against abscess induction, animals were vaccinated with either polysaccharide A or B, or the S. pneumoniae type 1 CP and challenged with heterologous and homologous polymers. Each polymer resulted in protection against abscess formation (Table 4).

In order to determine if the charged groups on these polysaccharides were responsible for mediating protection to abscess formation, chemical modifications of polysaccharide A were performed. Specific chemical modifications to polysaccharide A were performed to neutralize both the positively and negatively charged groups (as described in the above section on abscess induction) and the modified polysaccharide used to vaccinate animals for protection studies. Animals were vaccinated with N-acetylated polysaccharide A or reduced polysaccharide A and challenged with a native, unmodified polysaccharide A. In each case the chemically modified polysaccharides failed to protect animals against polysaccharide-induced abscess formation (Table 5, P is less than 0.05 compared with animals vaccinated with native polysaccharide A and challenged with polysaccharide A). This experiment demonstrated that the free amino and carboxyl groups in polysaccharide A are essential for polysaccharide-mediated protection against abscess formation.

TABLE 5

Effect of chemical modifications to PS A on induction of protection against abscess caused by B. fragiles polysaccharides.

| Polysaccharide vaccine+ (10 μg) | Challenge Polysaccharide (200 μ) | Number of rats with abscesses/total | P |
|---|---|---|---|
| PS A | PS A | 1/8 | — |
| PS A: N-acetylated (eliminates positive charge) | PS A | 8/10 | <0.005 |
| PS A: reduced (eliminates negative charge) | PS A | 7/10 | <0.05 |
| GBS Type 3 CP | PS A | 7/9 | <0.05 |
| GBS Type 3 CP | PS B | 8/9 | — |
| GBS Type 3 CP | S. pneumoniae Type 1 CP | 7/9 | — |
| S. pneumoniae Type 3 CP | PS A | 6/9 | — |
| S. pneumoniae Type 14 CP | PS A | 6/7 | — |

+Each group was compared with animals immunized with unmodified PS A and challenged with this same polysaccharide.

Another experiment was performed testing bacterial polysaccharides that either completely lacked charged groups or have only negatively charged substituents. Animals were vaccinated with the type III GBS CP and challenged with either polysaccharide A, polysaccharide B, or the S. pneumoniae type 1 CP. The type III GBS CP, which has one negatively charged group per repeating unit in a terminal sialic acid residue, failed to protect animals against challenge with each of the abscess inducing polymers (Table 5). Animals vaccinated with the type III S. pneumoniae CP (one negatively charged group per repeating unit) or the type 14 S. pneumoniae CP (no charged substituents in its repeating unit) also failed to protect against abscess formation induced by polysaccharide A (Table 5).

Example 3

Immune Response is T Cell Dependent

T Cell-Mediated Protection to Polysaccharide-Induced Abscesses

Animals were vaccinated as described above and were available for adoptive transfer experiments on week 6. Cell transfer experiments were performed as previously described. Shapiro, M. et. al., J. Immunol. 137:341–346 (1986) and Shapiro, M. at. al., J. Exp. Med. 154:1188–1197

(1982). Briefly, spleens were removed from vaccinated or naive rats and gently teased in RPMI medium supplemented with 5% fetal calf serum. Cells were counted using a Coulter FN Counter (Coulter Electronics Inc., Hialeah, Fla.) and were examined for viability by trypan blue exclusion. The preparation was enriched for T cells by passage over nylon wool columns. Purified T cells were then counted and adjusted to the appropriate cell number ($1 \times 10^7$/animal) prior to intra-cardiac transfer to animals (0.2 ml volume).

It was previously demonstrated that vaccination with the purified CPC protects against abscess formation following challenge with viable B. fragilis by a T cell dependent mechanism. Onderdonk J. Clin. Investigation 69:9–16 (1982). In the present experiments, we tested whether protection Against polysaccharide-induced abscesses is also T lymphocyte-dependent. Naive rats were administered purified T cells ($1 \times 10^7$ cells/animal) obtained from animals previously vaccinated with polysaccharide A. T cell recipients were then challenged with abscess-inducing polysaccharides (A, B or the type I S. pneumoniae CP). In each case, T cells from polysaccharide A-vaccinated animals protected naive animals against abscesses formed subsequent to homologous and heterologous polysaccharide challenge (Table 6, P is less than 0.05 compared with animals given T cells from saline-treated animals and challenged with native polysaccharide A). Rats receiving T cells obtained from animals immunized with type III GPS CP (no positively charged group) were not protected against abscesses following challenge with polysaccharide A (Table 6).

TABLE 6

T cell mediated protection against abscess formation by native and chemically modified polysaccharides.

| Polysaccharide Vaccine (10 μg) | Challenge Polysaccharide (200 μ) | Number of rats with abscesses/total | P value+ |
|---|---|---|---|
| saline | PS A | 7/8 | — |
| type III GBS | PS A | 4/5 | — |
| PS A | PS A | 0/8 | <0.05+ |
| PS A | PS B | 1/8 | <0.05+ |
| PS A | S. pneumo type 1 PS | 0/7 | <0.05+ |
| PS A (N-acetylated) | PS A | 7/9 | <0.005* |
| PS A (reduced) | ? S A | 6/9 | <0.05* |
| Vi | PS A | 7/9 | — |
| Vi (de-N-acetylated) | PS A | 2/8 | <0.05¶ |

+compared with animals given T cells from saline-immunized rats and then challenged with PS A
*compared with animals given T cells from PS A-immunized rats and then challenged with PS A
¶compared with animals given T cells from VI polysaccharide-immunized rats and then challenged with PSA.

Chemical Modification to Eliminate Oppositely Charged Groups on Polysaccharides that Induce T cell-dependent Protection against Abscess Induction To assess the role of the oppositely charged groups on polysaccharide A in T cell-mediated protection against abscess induction, animals were immunized with either N-acetylated polysaccharide A or carbodiimide reduced polysaccharide A and T cells from these animals administered to naive rats. T cells taken from animals vaccinated with the chemically modified versions of polysaccharide A failed to confer protection against challenge with unmodified polysaccharide A (Table 5, P is less than 0.05).

T Cell-Mediated Protection by a Polysaccharide Created to Contain Oppositely Charged Groups.

Additional adoptive T cell transfer experiments were performed in order to confirm that the presence of both positively and negatively charged groups in polysaccharides are required for protection to polysaccharide-mediated abscess formation. Chemical de-N-acetylation of the Vi capsular polysaccharide of S typhi, a homo polymer of galactaminuronic acid, was employed to convert this polysaccharide from a polymer that possessed one negatively charged carboxyl group per repeating unit to a saccharide that possessed one positively charged amino group and one negatively charged carboxyl group per repeating unit. In this experiment, T cells were harvested from the spleens of animals vaccinated with the unmodified or de-N-acetylated Vi polysaccharides and transferred to separate groups of naive rats. Each group of rats that received T cells was challenged with B. fragilis polysaccharide A. Rats receiving T-cells from animals vaccinated with the unmodified Vi polysaccharide were not protected against abscess induction by polysaccharide A, while animals receiving T cells from rats vaccinated with de-N-acetylated Vi polysaccharide were protected against abscess induction by polysaccharide A (Table 6, P is less than 0.05).

Example 4

Temporal Vaccination Experiment

Animals were vaccinated via the subcutaneous route with B. fragilis PS A lot p. 7 according four different time sequences.

Group 1—Time schedule A: 3 times per week for three weeks (MWF), with two boosts, Group 2—Time schedule B: 3 times per week for two weeks, with two boosts Group 3—Time schedule C: 3 times per week for one week, with two boosts Group 4—Time schedule D: 24 h before, 4 and 24 h after challenge.

Boosts were administered on Friday following vaccination schedule and Monday prior to challenge on Wednesday. Animals were challenged with an abscess-inducing dose of B. fragilis ($10^8$ cfu/animals).

Animals vaccinated via all four time schedules did not form abscesses following challenge with B. fragilis in this experiment.

Example 5

Oxidation and Reduction Technique for Providing a Hydroxymethyl Group

This entails first oxidizing the polymer with 0.01M sodium metaperiodate ($NaIO_4$) as previously described. Jennings, H. J., Lugowski, C. Immunochemistry of groups A, B and C meningococcal polysaccharide-tetanus toxiod conjugates, The Journal of Immunology, 123:1011–1018 (1981). This accomplishes selective creation of carbonyl groups (C=O) on the galactofuranose side-chain of the PS A repeating unit. The polysaccharide is treated for 90 minutes at room temperature in the dark. Ethylene glycol is then added to stop the reaction. The polysaccharide is then dialyzed against distilled water at 4° C. to remove excess glycol and periodate. This group is very amenable to reduction with a reducing agent such as sodium borohydride ($NaBH_4$) and will convert it to a hydroxymethyl group (CH₂OH). Approximately 2 mg of borohydride is added to this mixture following dialysis and incubated for two hours while stirring at room temperature. This mixture is then dialyzed against water as above to remove the excess borohydride.

Those skilled in the art will be able to recognize or ascertain with no more than routine experimentation numerous equivalents to the specific products and processes described above. Such equivalents are considered to be within the scope of the invention and are intended to be covered by the following claims in which we claim:

1. A method for inducing protection against abscess formation associated with infection comprising:
    administering to a subject in need of such protection a pharmaceutical preparation containing an effective amount, for inducing protection against abscess formation, of a polysaccharide formed of repeating units with each repeating unit being formed of a maximum of ten monosaccharides, wherein each repeating unit includes a free amino moiety and a negatively charged moiety selected from the group consisting of carboxyl, phosphate and phosphonate, and wherein the polysaccharide is free from dimerization as part of a *B. fragilis* capsular polysaccharide complex.

2. A method as in claim 1 wherein each repeating unit is formed of a maximum of five monosaccharides.

3. A method as in claim 1 wherein the polysaccharide is formed by the process of de-N-acetylation of a precursor polysaccharide.

4. A method as in claim 1 wherein the polysaccharide is formed by the process of reducing an imine group of a precursor polysaccharide.

5. A method as in claim 1 wherein the polysaccharide is *B. fragilis* capsular polysaccharide A.

6. A method as in claim 1 wherein the polysaccharide is *B. fragilis* capsular polysaccharide A, modified at the C-5 position of the furanoside to include a hydroxymethyl group.

7. A method as in claim 1 further comprising administering to the subject an amount of a cytokine effective for enhancing the induction of protection against abscess formation.

8. A method as in claims 1, 2, 3, 4, or 7 wherein the polysaccharide is a bacterial capsular polysaccharide.

9. A method for preparing a pharmaceutical for inducing protection against abscess formation associated with infection comprising:
    selecting a polysaccharide formed of repeating units with each repeating unit being formed of a maximum of ten monosaccharides, each repeating unit having at least one negatively charged moiety selected from the group consisting of carboxyl, phosphate and phosphonate, and having at least one N-acetyl moiety;
    de-N-acetylating the polysaccharide to convert said at least one N-acetyl moiety of each repeating unit to a free amino moiety; and
    mixing the de-N-acetylated polysaccharide with a pharmaceutically acceptable carrier.

10. A method as in claim 9 wherein the de-N-acetylated polysaccharide is mixed with the pharmaceutically acceptable carrier in amounts to form an effective dose for protecting a subject against abscess formation associated with infection.

11. A method as in claim 10 wherein the polysaccharide is a bacterial capsular polysaccharide.

12. A method as in claim 11 further comprising mixing the de-N-acetylated polysaccharide with a T-cell stimulating cytokine.

13. A method for preparing a pharmaceutical for inducing protection against abscess formation associated with infection comprising:
    selecting a polysaccharide formed of repeating units with each repeating unit being formed of a maximum of ten monosaccharides, each repeating unit having at least one negatively charged moiety selected from the group consisting of carboxyl, phosphate and phosphonate, and having at least one imine group;
    reducing the polysaccharide to convert the at least one imine group of each repeating unit to a free amino moiety; and
    mixing the reduced polysaccharide with a pharmaceutically acceptable carrier.

14. A method as in claim 13 wherein the de-N-acetylated polysaccharide is mixed with the pharmaceutically acceptable carrier in amounts to form an effective dose for protecting a subject against abscess formation associated with infection.

15. A method as in claim 14 wherein the polysaccharide is a bacterial capsular polysaccharide.

16. A method as in claim 14 further comprising mixing the reduced polysaccharide with a T-cell stimulating cytokine.

17. A pharmaceutical preparation which induces protection against abscess formation comprising:
    a pharmaceutically effective amount, for inducing protection against abscess formation, of a polysaccharide consisting essentially of a plurality of a repeating unit, with each repeating unit being formed of a maximum of ten monosaccharides, each repeating unit including a free amine moiety and a negatively charged moiety, selected from the group consisting of carboxyl, phosphate and phosphonate; and
    a pharmaceutically acceptable carrier, wherein said polysaccharide is free from dimerization as part of a *B. fragilis* polysaccharide complex and said polysaccharide is not selected from the group consisting of *Streptococcus pneumoniae* polysaccharide, *Trypanosoma cruzi* lipopeptidophosphoglycan and *Pseudomonas aeurignosa* Fisher immunotype 7O-antigen.

18. A pharmaceutical preparation as in claim 17 wherein the polysaccharide is a bacterial polysaccharide.

19. A pharmaceutical preparation as in claim 17 wherein the polysaccharide is *B. fragilis* capsular polysaccharide A free of dimerization with *B. fragilis* capsular polysaccharide B.

20. A pharmaceutical preparation as in claim 17 wherein the polysaccharide is *B. fragilis* capsular polysaccharide A which has been modified to contain a hydroxymethyl group and is free of dimerization with *B. fragilis* capsular polysaccharide B.

21. A pharmaceutical preparation as in claim 17 wherein the polysaccharide is *B. fragilis* capsular polysaccharide B and is free of dimerization with *B. fragilis* capsular polysaccharide A.

22. A pharmaceutical preparation as in claim 17 wherein each repeating unit is a monosaccharide carrying both the free amino and a negatively charged group.

23. A pharmaceutical preparation as in claim 17 wherein each repeating unit is a disaccharide comprised of a first and a second covalently linked monosaccharide in a 1–4 linkage and wherein the negatively charged group of each repeating unit is on the first monosaccharide of each repeating unit.

24. A pharmaceutical preparation as in claim 17 wherein each repeating unit is a trisaccharide comprised of a first, second and third monosaccharide and wherein the negatively charged moiety of each repeating unit is on the first monosaccharide of each repeating unit.

25. A pharmaceutical prepartion as in claim 24 wherein the free amino moiety of each repeating unit is also in the first monosaccharide of each repeating unit.

26. A pharmaceutical preparation as in claim 17 wherein each repeating unit is trisaccharide comprised of a first, second and third monosaccharide and wherein the third monosaccharide of each repeating unit is free of any amino or negatively charged moiety.

27. A pharmaceutical preparation as in claim 17 wherein each repeating unit is a pentasaccharide with a trisaccharide backbone characterisitic of B. fragilis capsular polysaccharide A.

28. A pharmaceutical preparation as in claim 17 wherein each repeating unit is a hexasaccharide with a trisaccharide backbone characteristic of B. fragilis capsular polysaccharide B.

29. A pharmaceutical preparation which induces protection against abscess formation comprising:

a pharmaceutically effective amount, for inducing protection against abscess formation, of a polysaccharide; and a pharmaceutically acceptable carrier, wherein the polysaccharide was prepared by the process of de-N-acetylation of a precursor polysaccharide that consists essentially of a plurality of a precursor repeating unit, to produce a plurality of a precursor repeating unit with each modified repeating unit having at least one N-acetyl moiety and one negatively charged moiety selected from the group consisting of carboxyl, phosphate and phosphonate, wherein at least one N-acetyl moiety is de-N-acetylated to form a free amino moiety.

30. A pharmaceutical preparation which induces protection against abscess formation comprising:

a pharmaceutically effective amount, for inducing protection against abscess formation, of a polysaccharide; and a pharmaceutically acceptable carrier, wherein the polysaccharide was prepared by the process of reducing a precursor polysaccharide that consists essentially of a plurality of a precursor repeating unit, to produce a plurality of a modified repeating unit with each precursor repeating unit having at least one imine moiety and one negatively charged moiety selected from the group consisting of carboxyl, phosphate and phosphonate, wherein at least one imine moiety is reduced to form a free amino moiety.

31. A pharmaceutical preparation which induces protection against abscess formation comprising:

a pharmaceutically effective amount, for inducing protection against abscess formation, of a polysaccharide formed of repeating units of a maximum of ten monosaccharides with each repeating unit including a free amino moiety and a negatively charged moiety selected from the group consisting of carboxyl, phosphate and phosphonate and wherein said polysaccharide is free of dimerization as part of a B. fragilis polysaccharide complex;

a cytokine that enhances T-cell response and is free of B-cell enhancing activity; and a pharmaceutically acceptable carrier.

* * * * *